United States Patent

Bigliani et al.

Patent Number: 5,928,285
Date of Patent: *Jul. 27, 1999

[54] ORTHOPAEDIC IMPLANT HAVING AN ARTICULATING SURFACE WITH A CONFORMING AND TRANSLATIONAL SURFACE

[75] Inventors: Louis U. Bigliani, Englewood, N.J.; Evan L. Flatow, New York, N.Y.; Delfreda L. Norman, Fort Wayne, Ind.

[73] Assignee: Bristol-Myers Squibb Co., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/866,628

[22] Filed: May 30, 1997

[51] Int. Cl.⁶ ........................................................ A61F 2/40
[52] U.S. Cl. ................................................. 623/19; 623/18
[58] Field of Search ................................. 623/19, 22, 18, 623/16, 20

[56] References Cited

U.S. PATENT DOCUMENTS

| | | | |
|---|---|---|---|
| 3,694,820 | 10/1972 | Scales et al. | 3/1 |
| 3,979,778 | 9/1976 | Stroot | 3/1.91 |
| 4,031,570 | 6/1977 | Frey | 3/1.912 |
| 4,106,130 | 8/1978 | Scales | 3/1.91 |
| 4,261,062 | 4/1981 | Amstutz et al. | 3/1.91 |

(List continued on next page.)

FOREIGN PATENT DOCUMENTS

| | | | |
|---|---|---|---|
| 0 339 530 A2 | 11/1989 | European Pat. Off. | A61F 2/36 |
| 0 617 934 A1 | 10/1994 | European Pat. Off. | A61F 2/40 |
| 2 210 793 | 6/1989 | United Kingdom | A61F 2/40 |
| WO 95/22302 | 8/1995 | WIPO | A61F 2/36 |
| WO 95/23566 | 9/1995 | WIPO | A61F 2/34 |
| 96/23458 | 8/1996 | WIPO | 623/20 |

OTHER PUBLICATIONS

Pros. Design Considerations in Total Shoulder Arthroplasty—E. Flatow—Seminars in Arthro.—vol. 6, No. 4—Oct. 1995.
Biomechanics of the Shoulder—Matsen—Basic Biomechanics of the Skeletal System—1980.
Articular Geometry and Contact Pressures in Total Shoulder Arthroplasty—Friedman & Draughn—No date available.
Modular Total Shoulder: Early Experience & Impressions—Fenlin et al.—Seminars in Arthro., vol. 1, No. 2—Oct. 1990.
Bio–Modular® Total Shoulder—Biomet, Inc.,—c1990.
Bio–Modular® Total Shoulder—Biomet, Inc.—c1989.
Flexible Bio–Modular™ Total Shoulder—Biomet, Inc.—No date available.
The BiAngular Shoulder—Biomet, Inc.—No date available.
The BiAngular Shoulder—Biomet, Inc.—JBJS, Feb. 1989.
Global Shoulder™—Issues at Hand: Designing for Implant Stability—Depuy Inc.—1995.
Issues at Hand: Will Your Implant Treat All Shoulder Indications?—Depuy Inc—1995.
Global Total Shoulder Arthroplasty System—Depuy Inc.—1992.

(List continued on next page.)

*Primary Examiner*—Michael J. Milano
*Assistant Examiner*—Tram A. Nguyen
*Attorney, Agent, or Firm*—Margaret L. Geringer

[57] ABSTRACT

The invention is directed to an orthopaedic implant for implantation into a bone at a joint. The orthopaedic implant 10 includes an articulating surface 20 for mating with a complementary implant 30. The orthopaedic implant includes a body 12 defining the articulating surface. The articulating surface 20 includes a conforming surface 22 bounded by a translational surface 24. The conforming surface 22 allows rotational movement between the articulating surface and the complementary implant, and the translational surface 24 allows rolling and translational movement between the articulating surface and the complementary implant. The conforming surface 22 is tangent at a periphery thereof to the translational surface 24.

36 Claims, 2 Drawing Sheets

U.S. PATENT DOCUMENTS

| | | | |
|---|---|---|---|
| 4,784,662 | 11/1988 | Müller | 623/22 |
| 4,865,605 | 9/1989 | Dines et al. | 623/19 |
| 4,911,723 | 3/1990 | Menschik | 623/23 |
| 4,919,670 | 4/1990 | Dale et al. | 623/19 |
| 4,964,865 | 10/1990 | Burkhead et al. | 623/19 |
| 4,986,833 | 1/1991 | Worland | 623/19 |
| 4,990,161 | 2/1991 | Kampner | 623/16 |
| 5,032,132 | 7/1991 | Matsen, III et al. | 623/19 |
| 5,080,673 | 1/1992 | Burkhead et al. | 623/19 |
| 5,108,440 | 4/1992 | Grundei et al. | 623/19 |
| 5,133,763 | 7/1992 | Mullers | 623/22 |
| 5,282,865 | 2/1994 | Dong | 623/19 |
| 5,314,479 | 5/1994 | Rockwood, Jr. et al. | 623/19 |
| 5,358,526 | 10/1994 | Tornier | 623/19 |
| 5,383,936 | 1/1995 | Kubein-Meesenburg et al. | 623/19 |
| 5,405,393 | 4/1995 | Falkenstrom | 623/18 |
| 5,405,402 | 4/1995 | Dye et al. | 623/22 |
| 5,489,309 | 2/1996 | Lackey et al. | 623/19 |
| 5,489,310 | 2/1996 | Mikhail | 623/19 |
| 5,549,680 | 8/1996 | Gordon | 623/18 |
| 5,593,448 | 1/1997 | Dong | 623/19 |
| 5,702,458 | 12/1997 | Burstein et al. | 623/20 |
| 5,723,018 | 3/1998 | Cyprien et al. | 623/21 |

OTHER PUBLICATIONS

Think Global—Depuy—JBJS, Nov. 1993.

Buechal–Pappas™ Total Shoulder System—Endotec, Inc.—Jul. 1991.

Hipokrat Bi–modular Shoulder System—JBJS, Feb. 1996.

The Intermedics Select® Shoulder System—c1990.

Atlas Modular & Neer II™—The Kirschner Integrated Shoulder System™—Kirschner Medical Corp.—JBJS, Oct. 1995.

Fenlin Total Shoulder—Zimmer, Inc.—c1988—Literature No. 97–4065–01.

Zimmer Total Shoulder II—Zimmer, Inc.—c1981, 1987—Literature No. 97–4040–01.

Encore Orthopedics—The Foundation Total Shoulder System—1997.

5,928,285

ORTHOPAEDIC IMPLANT HAVING AN ARTICULATING SURFACE WITH A CONFORMING AND TRANSLATIONAL SURFACE

BACKGROUND OF THE INVENTION

1. Field of the Invention

The present invention relates to orthopaedic implants, and, more particularly, to glenoid implants having an articulating surface.

2. Description of the Related Art

An orthopaedic implant for implantation at the shoulder joint typically includes a glenoid implant and a mating humeral implant. The glenoid implant is attached to a prepared glenoid or scapula, and the humeral implant is attached to a prepared humerus. The humeral implant usually includes a ball at an end thereof which engages and moves relative to an articulating surface in the form of a concave surface formed in the glenoid implant. The ligaments and muscles of the body surrounding such an orthopaedic implant maintain the humeral implant against the glenoid implant, while at the same time allowing relative movement therebetween.

A glenoid implant is typically formed with an articulating surface which is either fully conforming or fully non-conforming relative to the head of the humeral implant. A fully conforming articulating surface has the same spherical radius as the humeral head, and thereby allows relative rotational movement therebetween. However, with a fully conforming articulating surface, the periphery or edge of the articulating surface is loaded by the head of the humeral implant when the arm is moved to a large degree relative to the upper body (such as when the arm is placed over the head). This edge loading at the periphery of the articulating surface may result in permanent deformation of the glenoid implant over a period of time.

A glenoid implant having an articulating surface which is fully non-conforming relative to the humeral head allows both rotation and a limited extent of translation of the humeral head relative to the glenoid implant. Such a fully non-conforming articulating surface normally has a spherical radius which is greater than the spherical radius of the humeral head, thereby allowing the rotational as well as rolling and translational movement therebetween. However, such a fully non-conforming articulating surface may result in increased contact pressures between the humeral head and glenoid implant because of the relatively small surface area which is in contact therebetween at any point in time. Such increased contact pressures also may result in permanent deformation of the humeral head and/or articulating surface on the glenoid component over a period of time.

Also, U.S. Pat. No. 4,106,130 provides a glenoid or scapular implant having an articulating surface with a compound concave bearing surface including a cupped area bounded by an annular trough. The curvature of the cupped area and the transverse curvature of the troughed area each are no greater than the curvature of the rounded convex bearing surface of the humeral articular surface. The cupped area and the annular trough adjoin each other at an obtuse angle. Accordingly, the ball of the humeral component can rock or move away from the cupped area and into the troughed area such that loading occurs at the edge between the cupped area and the troughed area. Such edge loading at the periphery of the cupped area may result in physical damage to the glenoid implant over a period of time.

What is needed in the art is a glenoid implant which allows rotation of the humeral head relative to the articulating surface during normal movements of the arm relative to the upper body, and which allows a limited extent of rolling and translational movement of the humeral head relative to the glenoid implant during more extreme movements of the arm relative to the upper body.

SUMMARY OF THE INVENTION

The present invention provides an articulating surface on an orthopaedic implant for a joint, wherein the articulating surface includes a conforming surface which is bounded by and tangent to a non-conforming or translational surface.

The invention comprises, in one form thereof, an orthopaedic implant for implantation into a bone at a joint. The orthopaedic implant includes an articulating surface for mating with a complementary implant. The orthopaedic implant includes a body defining the articulating surface. The articulating surface includes a conforming surface bounded by a non-conforming or translational surface. The conforming surface has the same spherical radius as the mating surface of the complementary implant and allows rotational movement between the conforming surface and the complementary implant. The translational surface has a spherical radius which is greater than the spherical radius of the mating surface of the complementary implant, and thus allows rolling and translational movement between the non-conforming surface and the complementary implant. The conforming surface is tangent at a periphery thereof to the translational surface.

An advantage of the present invention is that both rotational and translational movement are allowed between the articulating surface of the orthopaedic implant and the bearing surface of the complementary implant.

Another advantage is that a smooth transition is provided between the conforming surface and the translational surface, thereby reducing loading at the transition therebetween.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
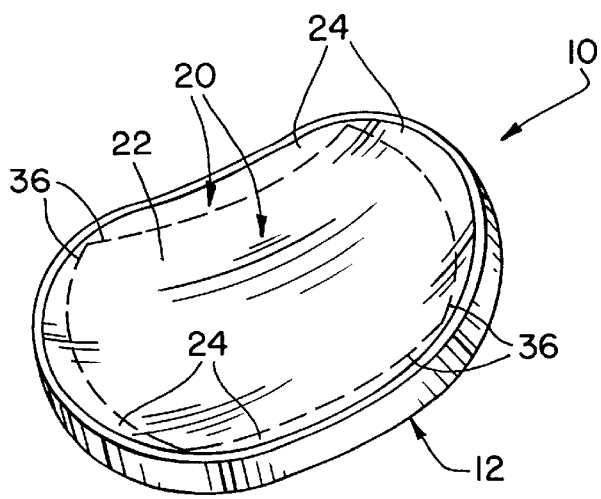
FIG. 1 is a perspective view of an embodiment of a glenoid implant of the present invention.
Figure 2:
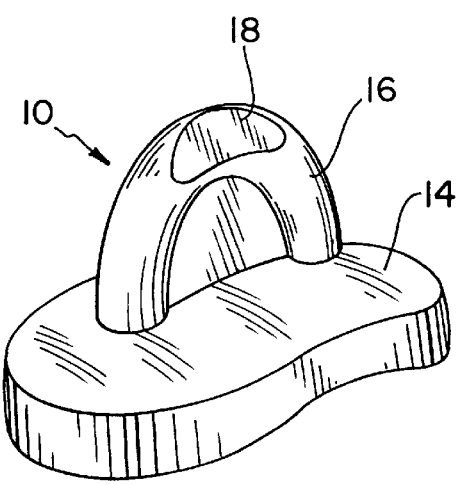
FIG. 2 is another perspective view of the glenoid implant shown in FIG. 1.
Figure 3:
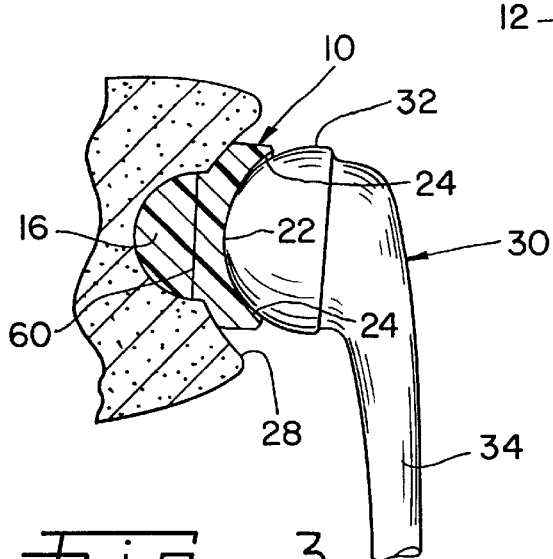
FIG. 3 is a side, partially sectioned view of the glenoid implant shown in FIGS. 1 and 2, when engaged with a prepared scapula and a humeral implant.
Figure 4:
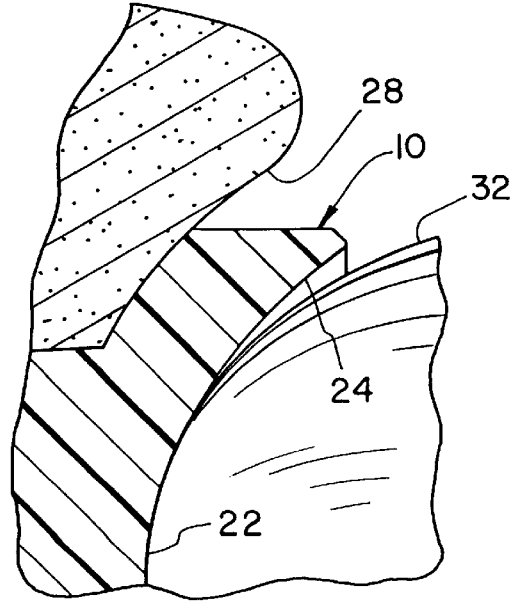
FIG. 4 is an enlarged, fragmentary view of the glenoid implant, scapula and humeral implant shown in FIG. 3.

Referring now to the drawings and more particularly to FIGS. 1 and 2, there is shown an orthopaedic implant in the form of a glenoid implant 10 for implantation into a glenoid or scapula at a shoulder joint. Glenoid implant 10 includes a body 12 with a convex surface 14 for placement against a prepared glenoid (FIGS. 3 and 4). A projection or keel 16 is attached to and extends from convex surface 14 of body 12. Keel 16 includes a pair of tapered portions 18, one of which is shown in FIG. 2. Tapered portions 18 provide for easier insertion of keel 16 into an opening which is prepared in the scapula. Glenoid implant 10 may be made from ultra high molecular weight polyethylene, and may include a metal X-ray wire 60, although any suitable materials may be utilized.

A concave articulating surface 20 is defined by body 12 on a side thereof which is generally opposite from keel 16. Articulating surface 20 is configured to engage the head of a complementary or humeral implant 30, as will be described in more detail hereinafter. Articulating surface 20 includes a conforming surface 22 which is bounded by a non-conforming or translational surface 24. Conforming surface 22 has the same spherical radius as the mating surface 31 of head 32 of humeral implant 30, and allows rotational movement between conforming surface 22 and the mating surface 31 of humeral implant head 32. Translational surface 24 has a spherical radius which is greater than the spherical radius of mating surface 31 of humeral implant 30, and thus allows rolling and translational movement between translational surface 24 and the humeral implant head. Articulating surface 20 is thus jointly defined by conforming surface 22 and non-conforming surface 24.

Referring now to FIGS. 3 and 4, glenoid implant 10 is shown in engagement with a prepared glenoid 28 and a humeral implant 30. Glenoid implant 10 and humeral implant 30 together define an orthopaedic implant assembly for use as a shoulder joint. Humeral implant 30 includes a head 32 which is attached to a stem 34. Stem 34, in known manner, is affixed to a prepared end of a humerus. The mating surface 31 of head 32 typically includes a portion of a sphere having a particular spherical radius. The humeral implant 30 may be made from a titanium alloy or cobalt-chrome alloy, although any suitable materials may be utilized.

As shown in FIGS. 3 and 4, conforming surface 22 has a shape which is substantially the same as the shape of the mating surface 31 of head 32 and thereby allows rotational movement between articulating surface 20 and head 32. Contrarily, translational surface 24 has a shape which is different from the shape of the mating surface 31 of head 32 and thereby allows rolling and translational movement between articulating surface 20 and head 32. According to the present invention, articulating surface 20 has a smooth transition between conforming surface 22 and translational surface 24, as shown in FIGS. 3 and 4. Particularly, conforming surface 22 is tangent to translational surface 24, and has a spherical radius which is smaller than the spherical radius of translational surface 24. In the embodiment shown in the drawings, conforming surface 22 has a spherical radius which is approximately between 2 and 6 mm smaller than the spherical radius of translational surface 24. Conforming surface 22 has a spherical radius of between approximately 20 and 28 mm, although it is not limited thereto. Likewise, translational surface 24 has a spherical radius of between approximately 22 mm and infinity (i.e., thereby generating a straight line), but is not limited thereto. For example, a particularly advantageous glenoid implant 10 in accordance with the present invention may have a conforming surface 22 with a spherical radius of 23 mm and a non-conforming surface 24 with a spherical radius of 26 mm to mate with a humeral head 32 having a 23 mm spherical radius. In addition, a glenoid implant in accordance with the present invention may also be provided with a conforming surface 22 having a spherical radius of 26 mm and a non-conforming surface 24 with a spherical radius of 29 mm to mate with a humeral head 32 having a 26 mm spherical radius. Various sized components may be offered, as desired.

Articulating surface 20 thus slightly angles away from head 32 around the periphery thereof as shown in FIGS. 3 and 4. Configured as such, head 32 of humeral implant 30 can move both in a rotational direction and translational direction relative to articulating surface 20 without the development of significant edge loading at the periphery of conforming surface 22 or significant contact pressures between head 32 and articulating surface 20.

Referring again to FIG. 1, the periphery of conforming surface 22 is indicated schematically by dashed line 36. Conforming surface 22 preferably defines at least 50 percent of the total surface area of articulating surface 20, and more preferably defines approximately 65 to 75 percent of the total surface area of articulating surface 20. Thus, the remainder of the total surface area of articulating surface 20 is defined by translational surface 24 disposed about the periphery of conforming surface 22. Articulating surface 20 is oblong or elongated in a direction generally parallel to keel 16. The conforming surface 22, as shown in FIG. 1, is oblong with the translational surface 24 disposed about the periphery thereof. However, the exact shape of articulating surface 20, the extent to which articulating surface 20 surrounds head 32, and other design considerations may be varied in known manner.

Figure 5:
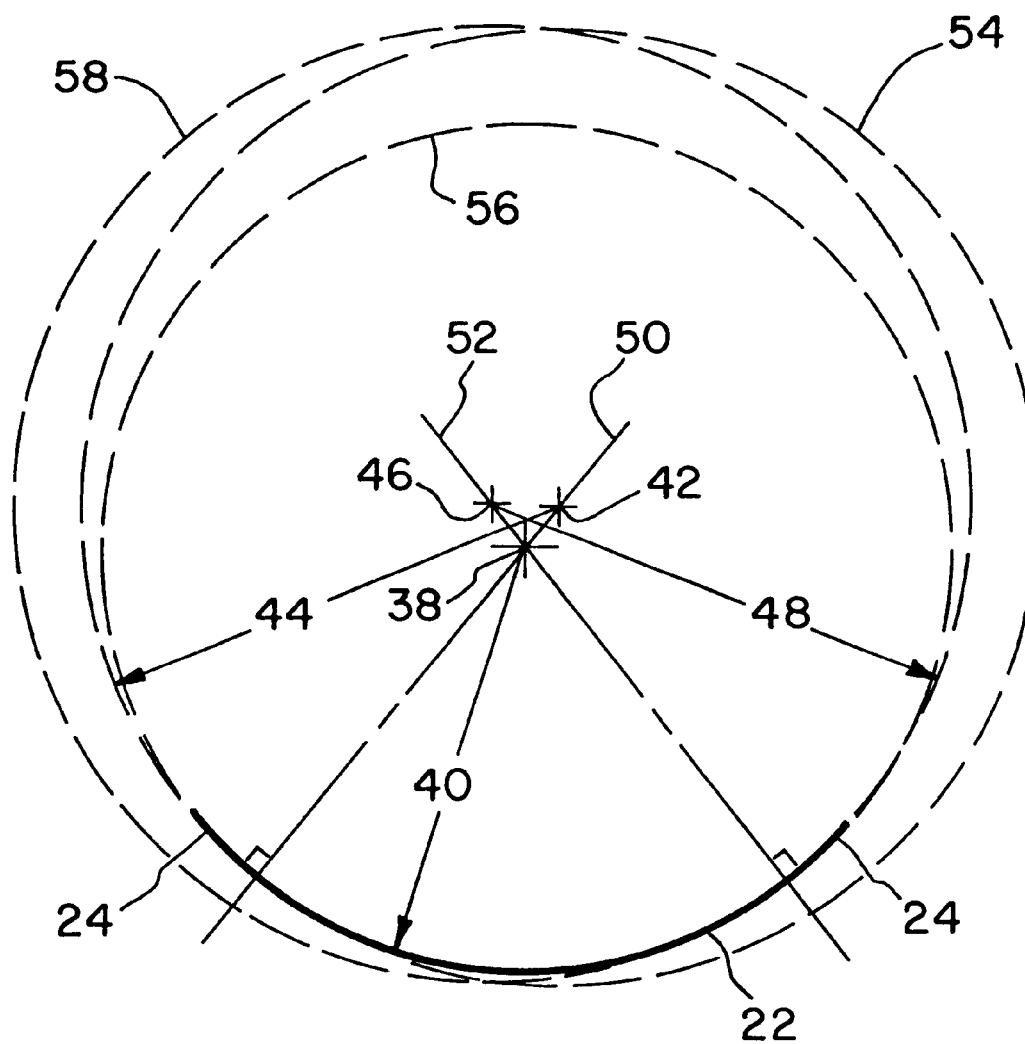
FIG. 5 is a schematic illustration of the curvature of the articulating surface on the glenoid implant shown in FIGS. 1–4.

Referring now to FIG. 5, there is shown a schematic representation of the curvatures of conforming surface 22 and translational surfaces 24 relative to each other. Conforming surface 22 has a spherical radius with a center point 38 and a length 40 of approximately 23 mm. Translational surface 24 to the left of FIG. 5 has a spherical radius with a center point 42 and a length 44 of approximately 26 mm. Similarly, translational surface 24 to the right of FIG. 5 has a spherical radius with a center point 46 and a length 48. A center line 50 extending through center point 42 and center point 38 extends through the edge of conforming surface 22 and is perpendicular to each of conforming surface 22 and translational surface 24 to the left of FIG. 5. Likewise, a center line 52 extending through center point 46 and center point 38 passes through the edge of conforming surface 22, and is perpendicular to each of conforming surface 22 and translational surface 24 at the point of contact therewith. For purposes of illustration, the remaining portion of the circles defining the left translational surface 24, conforming surface 22 and the right translational surface 24 are respectively identified by reference numbers 54, 56 and 58.

In the embodiment shown in the drawings, conforming surface 22 is disposed tangent to translational surface 24. However, it is also to be understood that conforming surface 22 may be disposed other than tangent to translational surface 24 such that a smooth transition exists therebetween. For example, it may be desirable for a particular application to provide articulating surface 20 with a smooth transition between conforming surface 22 and translational surface 24 such as may be obtained using a least squares numerical analysis fit therebetween.

Moreover, in the embodiment shown, conforming surface 22 is substantially entirely bounded by translational surface 24 at the periphery thereof. However, it is also to be understood that translational surface 24 need not entirely surround conforming surface 22, and may only be disposed adjacent to one or more sides of conforming surface 22.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A combination shoulder joint comprising an orthopaedic implant and a complementary implant, said orthopaedic implant including an articulating surface for mating with the complementary implant, said complementary implant including a mating surface having a first curvature generated by a first spherical radius, and said orthopaedic implant comprising:

a body defining said articulating surface, said articulating surface including a conforming surface having a periphery and bounded on at least two sides by a non-conforming translational surface, said conforming surface having a second curvature generated by a second spherical radius which is substantially the same as the first spherical radius of the complementary implant, said conforming surface allowing rotational movement between said articulating surface of the orthopaedic implant and the mating surface of the complementary implant, and said translational surface having a shape which is different from said second spherical radius, said shape comprising a part-spherical shape having a third curvature generated by a third spherical radius greater than said first spherical radius and said second spherical radius thereby allowing rolling and translational movement between said articulating surface and the complementary implant, said conforming surface being tangent, at said periphery, to said translational surface where said conforming surface is bounded by said translational surface.

2. The combination of claim 1, wherein said conforming surface comprises at least 50 percent of the area of said articulating surface.

3. combination of claim 1, wherein said conforming surface comprises approximately 65 to 75 percent of the area of said articulating surface.

4. The combination of claim 1, wherein the spherical radius of said conforming surface is between approximately 20 and 28 mm.

5. The combination of claim 1, wherein the spherical radius of said conforming surface is approximately 23 mm, and said translational surface has a spherical radius of approximately 26 mm.

6. The combination of claim 1, wherein the spherical radius of said conforming surface is approximately 26 mm, and said translational surface has a spherical radius of approximately 29 mm.

7. The combination of claim 1, wherein the translational surface has a spherical radius which is at least about 2 to 6 mm larger than the second spherical radius of the conforming surface.

8. The combination of claim 1, wherein said conforming surface and said translational surface each comprise a concave surface and said mating surface of the complementary implant comprises a convex surface.

9. The combination of claim 1, wherein said orthopaedic implant comprises a glenoid implant, and the complementary implant comprises a humeral implant.

10. The combination of claim 1, wherein said second curvature of said conforming surface comprises a concave surface and said first curvature generated by said first spherical radius of the complementary implant comprises a convex surface.

11. The combination of claim 1, wherein said conforming surface is substantially entirely bounded by said translational surface.

12. The combination of claim 1, wherein the articulating surface of the orthopaedic implant is symmetrical about a midline thereof.

13. A combination shoulder joint comprising a humeral component and a glenoid implant, one of said humeral component or glenoid implant comprising an orthopaedic implant and the other of said humeral component or glenoid implant comprising a complementary implant, said orthopaedic implant including an articulating surface for mating with a surface of the complementary implant, said orthopaedic implant comprising:

a body defining said articulating surface, said articulating surface including a conforming surface bounded on at least two sides by a translational surface, said conforming surface having a shape which is the same as the surface of the complementary implant and thereby allows rotational movement between said articulating surface and the surface of the complementary implant, and said translational surface having a shape which is different from the surface of the complementary implant and thereby allows rolling and translational movement between said articulating surface and the surface of the complementary implant, said articulating surface having a smooth transition between said conforming surface and said translational surface.

14. The combination of claim 13, wherein said conforming surface is tangent to said translational surface at said smooth transition.

15. The combination of claim 13, wherein said conforming surface comprises at least 50 percent of the area of said articulating surface.

16. The combination of claim 13, wherein said conforming surface comprises approximately 65 to 75 percent of the area of said articulating surface.

17. The combination of claim 10, wherein said conforming surface has a curvature generated by a spherical radius of between approximately 20 and 28 mm, and said translational surface is a non-conforming surface generated by a spherical radius greater than the spherical radius of said conforming surface.

18. The combination of claim 13, wherein said conforming surface has a curvature generated by a spherical radius of approximately 23 mm, and said translational surface has a different curvature generated by a different spherical radius of approximately 26 mm.

19. The combination of claim 13, wherein said conforming surface has a curvature generated by a spherical radius of approximately 26 mm, and said translational surface has a different curvature generated by a different spherical radius of approximately 29 mm.

20. The combination of claim 13, wherein said conforming surface is concave and said surface of the complementary implant is convex and said conforming surface has a curvature generated by a spherical radius which is the same as a spherical radius of said surface of the complementary implant, and wherein said translational surface is concave and has a different curvature generated by a different spherical radius that is greater than the spherical radius of said surface of the complementary implant.

21. The combination of claim 13, wherein the conforming surface has a curvature generated by a spherical radius and said translational surface has a different curvature generated by a different spherical radius, wherein the spherical radius of the conforming surface is smaller than the different spherical radius of the translational surface.

22. The combination of claim 13, wherein the translational surface has a curvature generated by a spherical radius which is at least about 2 to 6 mm larger than a different spherical radius of the conforming surface which generates a different curvature.

23. The combination of claim 13, wherein the body further defines an attachment surface having at least one projection extending therefrom.

24. The combination of claim 23, wherein said at least one projection comprises a keel extending from said attachment surface which is on a side of the body generally opposite from said articulating surface.

25. The combination of claim 13, wherein the conforming surface is oblong with the translational surface disposed thereabout.

26. The combination of claim 25, wherein said oblong conforming surface has a plurality of interconnected sides, and wherein said translational surface is disposed about at least a portion of two of said plurality of sides.

27. The combination of claim 26, wherein said translational surface is disposed about at least a portion of each of said plurality of sides.

28. The combination of claim 25, wherein said conforming surface is substantially entirely bounded by said translational surface.

29. The combination of claim 13, wherein said orthopaedic implant comprises a glenoid implant, and the complementary implant comprises a humeral implant.

30. The combination of claim 13, wherein said conforming surface is substantially entirely bounded by said translational surface.

31. A combination shoulder joint comprising a humeral component and a glenoid implant, one of said humeral component or glenoid implant comprising an orthopaedic implant and the other of said humeral component or glenoid implant comprising a complementary implant, said orthopaedic implant including an articulating surface for mating with a surface of the complementary implant, said orthopaedic implant comprising:
    a body defining said articulating surface, said articulating surface including a conforming surface bounded on at least two sides by a translational surface, said conforming surface having a shape which is the same as the surface of the complementary implant and said translational surface having a shape which is different from the surface of the complementary implant, said conforming surface being tangent to said translational surface.

32. An orthopaedic implant assembly for use as a shoulder joint, said orthopaedic implant assembly comprising:
    a humeral implant including a head; and
    a glenoid implant including a body with an articulating surface for mating with said head;
        wherein one of said articulating surface and said head includes a conforming surface bounded on at least two sides by a translational surface, said conforming surface having a shape which is the same as a mating surface of the other of said articulating surface and said head allowing rotational movement between said glenoid implant and said head, and said translational surface having a shape that is different from the mating surface allowing rolling and translational movement between said glenoid implant and said head, said conforming surface being tangent at a periphery thereof to said translational surface.

33. A combination shoulder joint comprising an orthopaedic implant and a complementary implant, said orthopaedic implant including an articulating surface for mating with the complementary implant, said complementary implant including a mating surface having a first curvature generated by a first spherical radius, and said orthopaedic implant comprising:
    a body defining said articulating surface, said articulating surface including a conforming surface having a periphery bounded on at least two sides by a non-conforming translational surface, said conforming surface having a second curvature generated by a second spherical radius which is substantially the same as the first spherical radius of the complementary implant, said conforming surface allowing rotational movement between said articulating surface and the complementary implant, and said translational surface having a third curvature generated by a third spherical radius which is larger than said first and second spherical radii thereby allowing rolling and translational movement between said articulating surface and the complementary implant, said conforming surface being tangent at said periphery to said translational surface where said conforming surface is bounded by said translational surface.

34. A combination shoulder joint comprising a humeral component and a glenoid implant, one of said humeral component or glenoid implant comprising an orthopaedic implant and the other of said humeral component or glenoid implant comprising a complementary implant, said orthopaedic implant including an articulating surface for mating with a surface of the complementary implant, said complementary implant including a mating surface having a first curvature generated by a first spherical radius, and said orthopaedic implant comprising:
    a body defining said articulating surface, said articulating surface including a conforming surface bounded on at least two sides by a translational surface, said conforming surface having a shape having a second curvature which is generated by a second spherical radius which is the same as the first spherical radius of the complementary implant and thereby allows rotational movement between said articulating surface and the surface of the complementary implant, and said translational surface having a non-conforming surface generated by a third radius which is different from said first and second spherical radii and thereby allows rolling and translational movement between said articulating surface and the surface of the complementary implant, said articulating surface having a smooth transition between said conforming surface and said translational surface.

35. An orthopaedic implant assembly for use as a shoulder joint, said orthopaedic implant assembly comprising:
    a humeral implant including a head; and
    a glenoid implant including a body with an articulating surface for mating with said head;
        wherein one of said articulating surface and said head includes a conforming surface having a periphery bounded on at least two sides by a translational surface, said conforming surface having a shape having a first curvature which is generated by a first spherical radius which is substantially the same as a second spherical radius which generates a second curvature of a mating surface of the other of said articulating surface and said head allowing rotational movement between said glenoid implant and said head, and said translational surface having a shape having a third curvature generated by a third spherical radius that is different from the first and second spherical radii, the translational surface allowing rolling and translational movement between said glenoid implant and said head, said conforming surface being tangent at said periphery to said translational surface where said conforming surface is bounded by said translational surface.

36. The orthopaedic implant assembly of claim 33, wherein said conforming surface bounded on at least two sides by said translational surface is included on the glenoid implant, and wherein the articulating surface of said glenoid implant is concave and wherein said third spherical radius is greater than the first and second spherical radii.

* * * * *